United States Patent [19]

Haber et al.

[11] Patent Number: 5,287,850
[45] Date of Patent: Feb. 22, 1994

[54] TIMING AND VELOCITY CONTROLLED POWERED PHARMACEUTICAL INHALER

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 747,375

[22] Filed: Aug. 20, 1991

[51] Int. Cl.$^5$ ............................................. A61M 15/00
[52] U.S. Cl. ............................ 128/203.21; 128/203.15
[58] Field of Search ...................... 128/203.15, 203.21, 128/200.14, 200.22

[56] References Cited

U.S. PATENT DOCUMENTS

| | | | |
|---|---|---|---|
| 238,388 | 3/1881 | Heine | 128/200.22 |
| 460,458 | 9/1891 | Bates | 128/200.14 |
| 905,087 | 11/1908 | Mallory | 128/200.22 |
| 923,822 | 6/1909 | Dorment | 128/200.22 |
| 1,838,873 | 12/1931 | Scott | 128/200.22 |
| 2,079,587 | 5/1937 | Aronson | 128/200.22 |
| 3,144,867 | 8/1964 | Trupp et al. | 128/200.22 |
| 3,155,573 | 11/1964 | Fowler | 128/200.22 |
| 3,425,414 | 2/1969 | La Roche | 128/203.21 |
| 3,518,992 | 7/1970 | Altounyan et al. | 128/203.15 |
| 3,669,113 | 6/1972 | Altounyan et al. | 128/203.15 |
| 3,888,252 | 6/1975 | Side et al. | 128/203.21 |
| 3,888,253 | 6/1975 | Watt et al. | 128/203.21 |
| 3,971,377 | 7/1976 | Damani | 128/203.21 |
| 4,116,195 | 9/1978 | James | 128/203.15 |
| 4,117,844 | 10/1978 | James | 128/203.15 |
| 4,338,931 | 7/1982 | Cavazza | 128/203.15 |
| 4,565,301 | 1/1986 | Hubbard et al. | 128/203.21 |
| 4,811,731 | 3/1989 | Newell et al. | 128/203.15 |

FOREIGN PATENT DOCUMENTS 9007351 7/1990 Denmark .

OTHER PUBLICATIONS

McGraw-Hill Encyclopedia of Science and Technology, 5th Edition, "Atomization," pp. 858-862.

Spinhaler ® Turbo-Inhaler instruction leaflet, Fisons Corporation.
Product literature, "The Spinhaler", U.S. Patents 3,518,992 and 3,669,113, Rev. Apr. 1983.
Product literature, "Boehringer Ingelheim", Jul. 1988.
Product literature, "Rotahaler", Sep. 1988.
Product literature, "Turbuhaler", Dec. 1987.
Product literature, "Diskhaler".
Product literature, "Proventil Inhaler", Rev. Aug. 1988.
Product literature, "Novo Nordisk Magazine", Jun. 1991.

Primary Examiner—Edgar S. Burr
Assistant Examiner—Aaron J. Lewis
Attorney, Agent, or Firm—Townsend and Townsend Khourie and Crew

[57] ABSTRACT

A powdered pharmaceutical inhaler (2) includes, broadly, an air pressurization chamber (6), housing a piston and cylinder arrangement for providing a charge of pressurized air to the air pressurization chamber, and an inhalation chamber (4), including a mouthpiece region (16) and a pharmaceutical region (92) containing the pharmaceutical (156). The inhaler is actuated by inhaling on the mouthpiece region which automatically opens a fluid pathway between the air pressurization chamber and the supply of powered pharmaceutical. When this occurs the air rushes from the air pressurization chamber through the powered pharmaceutical, thus entraining the powdered pharmaceutical in an airstream, the entrained pharmaceutical being inhaled into the lungs of the user. The inhaler is thus activated by the inhalation by the user and is provided a pneumatic boost from the pressurized air in the air pressurization chamber. The invention is designed to be used with replaceable pharmaceutical-containing cartridges (12). The cartridges are mounted to the mouthpiece region of the inhalation chamber and contain the powdered pharmaceutical. Thus, after each use the cartridge is disposed of so that all surfaces which may be clogged or otherwise contaminated by the powdered pharmaceutical, saliva and so forth, can be disposed of.

16 Claims, 7 Drawing Sheets

TIMING AND VELOCITY CONTROLLED POWERED PHARMACEUTICAL INHALER

BACKGROUND OF THE INVENTION

Certain pharmaceuticals can be administered in powdered form through inhalation of the powdered pharmaceutical into the lungs. This type of pharmaceutical delivery has several advantages. It eliminates the requirement for the use of syringes and needles, which many patients are uncomfortable with. Also, certain pharmaceuticals have a relatively short shelf life when in liquid form. Therefore, administration in powdered form eliminates the necessity to reconstitute the pharmaceutical with a liquid carrier.

Although not all pharmaceutical products are suitable for it being administered in a powdered form, many pharmaceuticals have been formulated for inhalation into the lungs. For example, Novo Nordisk of Bagsvaerd, Denmark, sells a nasal insulin preparation which is inhaled by the user. Other types of pharmaceuticals are administered in powdered form as well. Another pharmaceutical for oral inhalation by asthmatic patients is sold by Glaxo of Bern, Switzerland. The medication is delivered by a device, sold as the DISKHALER ®, which has a rotatable disk with a number of regions containing the pharmaceutical. The disk is rotated to position one of the pharmaceutical-containing packets in line with a needle; the needle punctures the packet to allow the pharmaceutical to be inhaled. Another type of powdered pharmaceutical delivery device is sold by Fisons Corporation of Bedford, Mass., under the trademark SpinHaler ®. It uses a gel capsule containing the powdered pharmaceutical. The capsule is pierced by a needle which allows the pharmaceutical to be inhaled through the mouth.

One of the problems with prior art powdered pharmaceutical delivery devices when the device is reused, as is normal. The powdered pharmaceutical often clings to, coats or even cakes onto surfaces of the device. The surfaces, which often have been moistened by the user's breath, can become contaminated; the contaminated surfaces can create health problems during subsequent use due to the bacterial contamination.

SUMMARY OF THE INVENTION

The present invention is directed to a powdered pharmaceutical inhaler which uses compressed gas, typically compressed air, to aid the proper delivery of the powdered pharmaceutical into the user's lungs, together with delivery of the pharmaceutical automatically and inherently timed to the initial inhalation of the user. The device is constructed so that contaminated surfaces are part of a replaceable cartridge to reduce or eliminate the contamination problems associated with the prior art multiple use powdered pharmaceutical delivery devices.

The powdered pharmaceutical inhaler includes, broadly, an air pressurization chamber and an inhalation chamber. The pressurization chamber preferably includes a plunger and cylinder arrangement for providing a charge of pressurized air to the air pressurization chamber. The inhalation chamber includes a mouthpiece region and a pharmaceutical region containing a supply of the powdered pharmaceutical. When the user inhales on the mouthpiece region, a fluid pathway between the air pressurization chamber and the supply of powered pharmaceutical is automatically opened. When this occurs the air rushes from the air pressurization chamber through the powered pharmaceutical thus entraining the powdered pharmaceutical in an airstream which is inhaled into the lungs of the user. The inhaler is thus activated by the initial inhalation by the user and provides a pneumatic boost from the pressurized air in the air pressurization chamber.

The invention is designed to be used with replaceable cartridges. One of the cartridges is mounted to the mouthpiece region of the inhalation chamber and contains the powdered pharmaceutical. After each use, all surfaces which have been exposed to the powdered pharmaceutical, especially in conjunction with the user's breath and saliva, and thus which may be clogged or contaminated, can be disposed of.

One of the main advantages of the invention is its simplicity and effectiveness. The user removes the cap from the inhaler and inserts a new cartridge, which contains a capsule with the powdered pharmaceutical, into the end of the inhalation chamber. The user then grasps the end of the plunger and reciprocates it once to create the volume of pressurized air within the pressurization chamber. After placing the mouthpiece into his or her mouth, the user inhales causing a partial vacuum within the inhalation chamber; this moves the trigger disk towards the user to its open position to open the pathway from the pressurization chamber to the powdered pharmaceutical. The sudden rush of air into the powdered pharmaceutical disperses the powdered pharmaceutical into the air stream which is being inhaled into the user's lungs.

It is important that the speed and volume of the pressurized air which is created be appropriate to the particular pharmaceutical, both as to type and amount used. If the speed of the air entering the user's mouth is too low, too much of the pharmaceutical will end up on the user's tongue and not be properly absorbed. If the speed is too fast, the powered pharmaceutical can be driven against the walls of the user's throat, and again not properly absorbed. The volume of air and the pressures produced can be easily changed by changing the size of the piston and cylinder arrangement of the pressurization chamber.

Other features and advantages of the invention will appear from the following description in which the preferred embodiment has been set forth in detail in conjunction with the accompanying drawings.

DESCRIPTION OF THE PREFERRED EMBODIMENT

Figure 1:
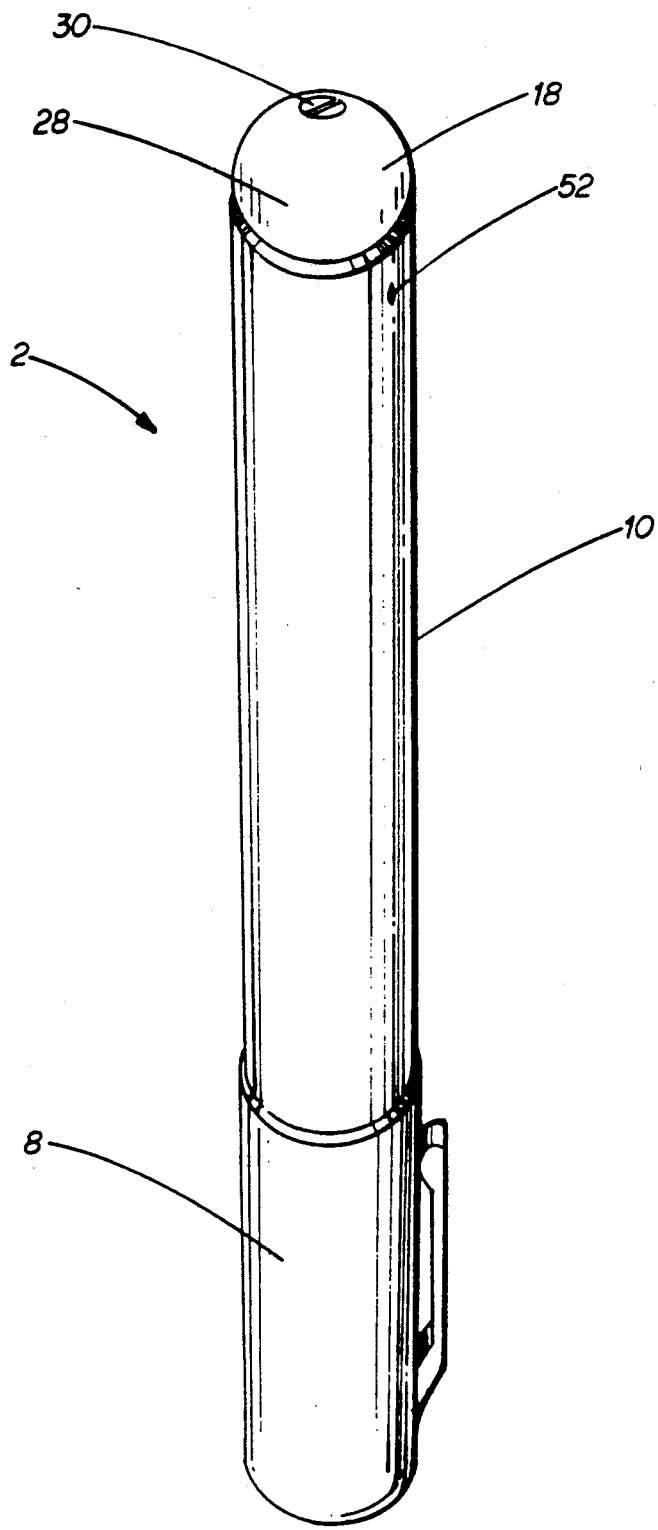
FIG. 1 is an isometric view of a powdered pharmaceutical inhaler made according to the invention.
Figure 3A:
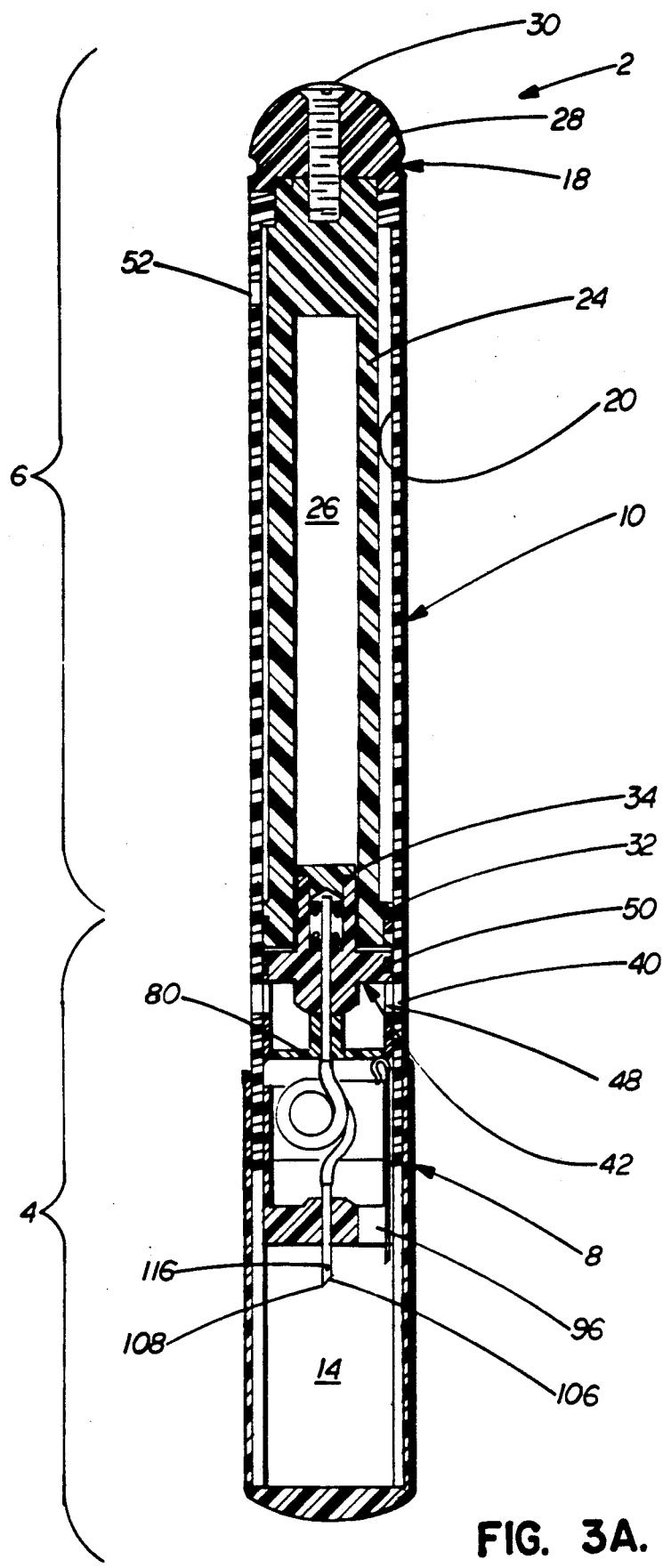
FIG. 3A is a cross-sectional view of the inhaler of the FIG. 1 with the cap in place prior to mounting a pharmaceutical cartridge within the body of the inhaler.
Figure 3B:
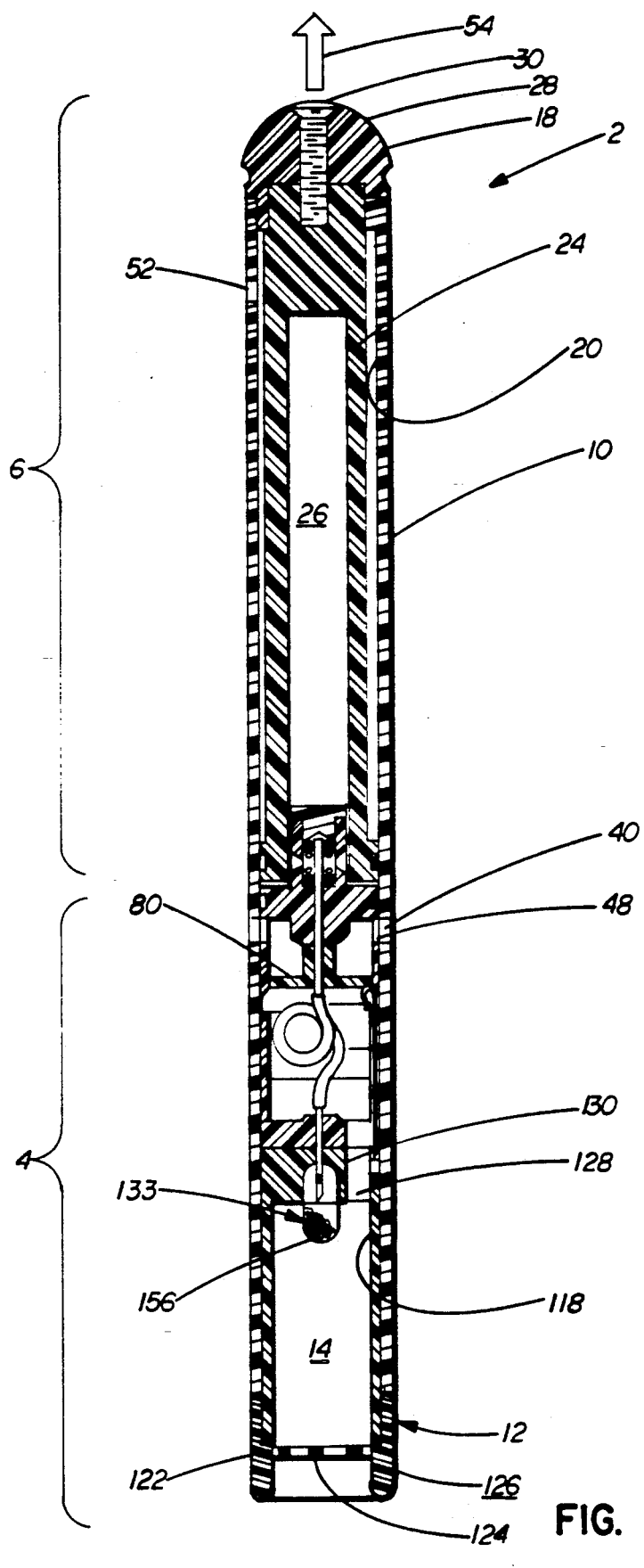
FIG. 3B illustrates the inhaler of FIG. 3A with the cap removed and a pharmaceutical cartridge mounted in the mouthpiece end of the body.
Figure 3C:
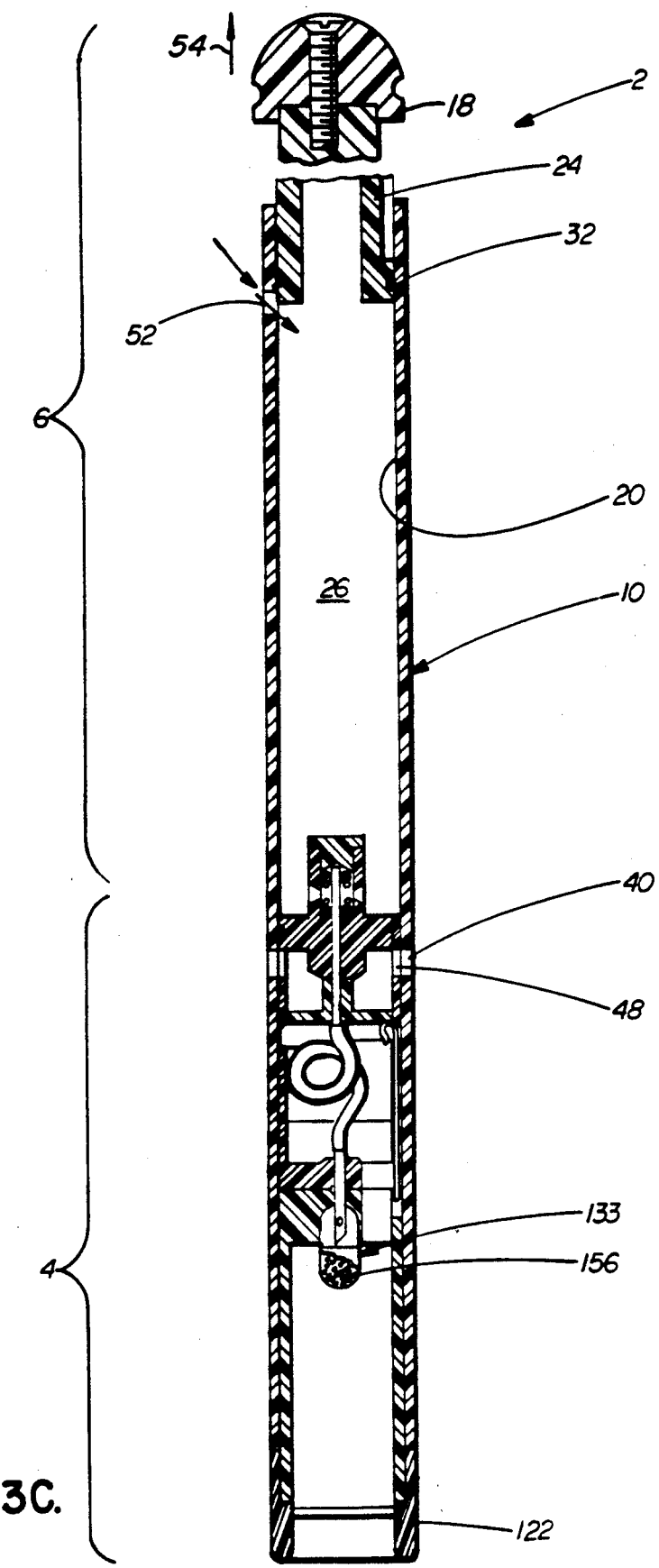
FIG. 3C shows the inhaler of FIG. 3B with the plunger withdrawn to a position with the piston adjacent a vent opening in the body to permit the entrance of air into the pressurization chamber.
Figure 3D:
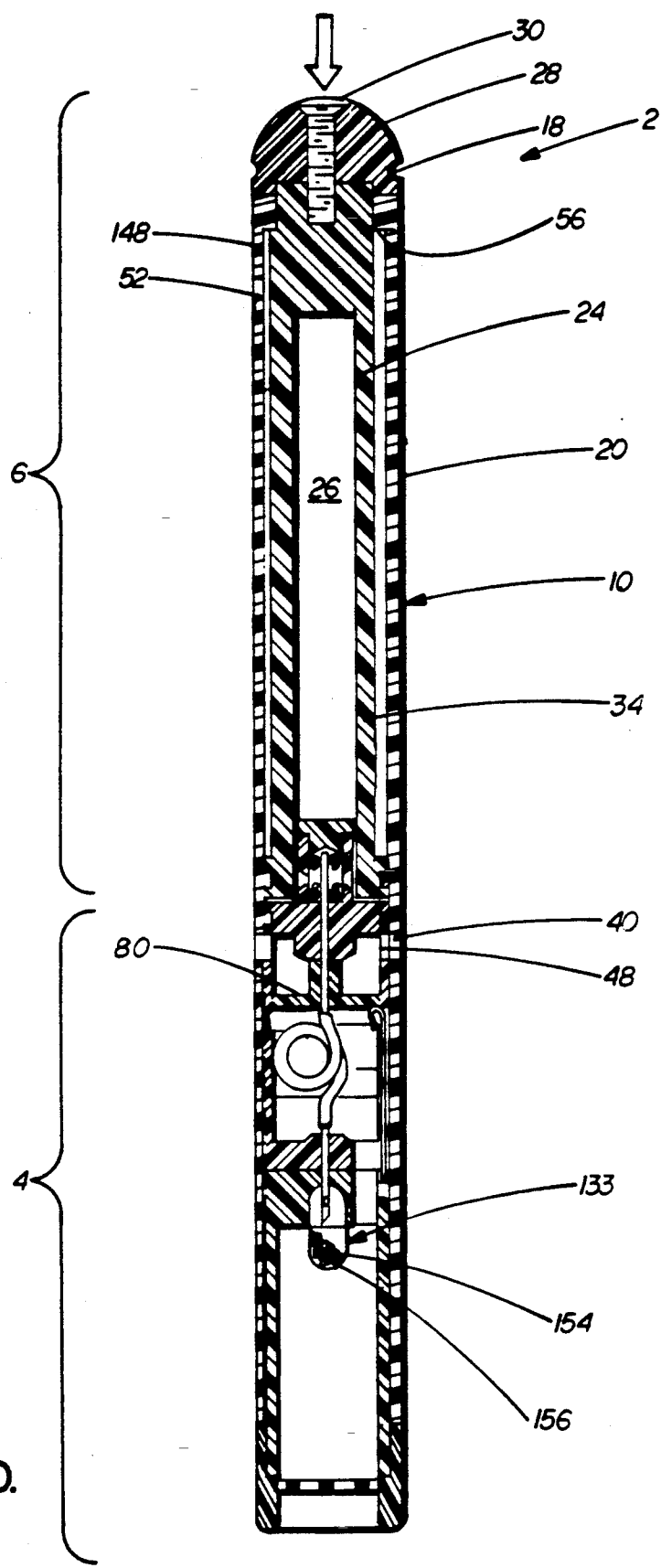
FIG. 3D shows the inhaler of FIG. 3C with the plunger backed in its retracted position, thus creating a volume of pressurized air within the pressurization chamber.

FIG. 1 illustrates an inhaler 2 made according to the invention in its pre-use condition. Inhaler 2 is typically about 14 cm. long and having a diameter of about 1.4 cm. and is designed to be pen-like in appearance for enhanced user acceptability.

Referring the reader now to FIGS. 2, 3A and 3B, inhaler 2 is shown to include generally an inhalation chamber 4 and a pressurization chamber 6. FIGS. 1 and 3A illustrates inhaler 2 with a cap 8 mounted to one end of an elongate tubular body 10. FIG. 3B illustrates inhaler 2 but with cap 8 removed and a pharmaceutical cartridge 12, also shown in FIG. 2, mounted within the interior 14 of body 10 at the mouthpiece end 16 of body 10. Both cap 8 and pharmaceutical cartridge 12 are illustrated in FIG. 2; however, both are not usually assembled to body 10 at the same time. Cap 8 could, however, be mounted over mouthpiece end of 16 of body 10 with pharmaceutical cartridge 12 in position if desired.

Pressurization chamber 6 includes a plunger 18 which reciprocates within a cylinder 20 defined by the pressurization end 22 of body 10. Plunger 18 includes an elongate stem 24 having a hollow interior 26 and a pull knob 28 secured to one end by a screw 30. Stem 24 has an integrally formed piston 32 at its other end 34. Piston 32 includes an 0-ring 36 which provides a good seal within cylinder 20. Cylinder 20 is sealed at one end 38 just to one side of a series of openings 40 formed in body 10 by a valve assembly 42. Valve assembly 42 includes a valve hosing 44 having a tubular end 46 with openings 48, which are positioned to coincide with openings 40 in body 10. Valve assembly 42 is held into place by the frictional engagement of an 0-ring 50, which fits within a groove 51 formed in valve housing 44, with cylinder 20 at end 38. Valve assembly 42 could also be permanently affixed within cylinder 20 if desired.

Body 10 has a vent 52 at one end 53 of body 10. Vent 52 permits air to enter cylinder 20 when plunger 18 is moved in the direction of arrow 54, as shown in FIG. 3C. The movement of plunger 18 in the direction of arrow 54 is limited by the engagement of piston 32 with annular shoulder 56 at end 53 of body 10.

The return of plunger 18 to the retracted position of FIGS. 3A and 3B causes pressurized air to be created within hollow interior 26 of stem 24. The degree of pressurization is controlled by sizing hollow interior 26. Thus, the size of hollow interior 26, as well as the length of stroke of piston 32, can be varied to accommodate different amounts and types of pharmaceuticals.

Valve assembly 42 also includes a plug 58 which seals a bore 60 formed in valve housing 44. Plug 58 also positions a pair of sealing O-rings 62, 64 on either side of a hollow sleeve 66. Sleeve 66 and valve housing 44 include aligned openings 68, 70, which permit fluid flow from hollow interior 26 of stem 24 to the hollow interior 72 of sleeve 66. Valve assembly 42 also includes an axially movable hollow tube 74, which passes through valve housing 44 with the open end 76 of hollow tube 74 being normally positioned adjacent plug 58 and sealingly engaged by O-rings 62 and 64. Accordingly, in the position of FIGS. 3A-3C, open end 76 is sealed from cylinder 20 and hollow interior 26 by O-ring 62.

Hollow tube 74 can reciprocate freely within valve housing 44. Hollow tube is fixed within the central bore 78 of a trigger disc 80, such as using a suitable adhesive. The movement of trigger disc 80, and hollow tube therewith, in the direction of arrow 54 is limited by the abutment of the trigger disc with valve housing 44 as shown in FIG. 3A. The movement of trigger disc 80, and hollow tube 74 therewith, in the direction opposite of arrow 54 is limited by the engagement of trigger disc 80 with the end 82 of a trigger disc return rod 84. Trigger disc return rod 84 slides within a groove 86 formed in an axilly extending finger 88 of a guide 90. Guide 90 is fixed within the interior 14 of body 10 at one end 92 of inhalation chamber 4 adjacent openings 40, such as using a suitable adhesive, a fiction fit or through ultrasonic welding techniques. The tip 94 of return rod 84 is positioned so that it extends below the end 96 of guide 90 for reasons discussed below with reference to the pharmaceutical cartridge 12.

The other end 98 of hollow tube 74 is connected to a hollow flexible tube 100 at one end 102 of tube 100. The other end 104 of tube 100 is connected to an open end 107 of a hollow needle 106 having a sharpened tip 108. Needle 106 is secured within a axial bore 110 formed in a centrally positioned hub 112 of guide 90. Hub 112 is positioned by three radially extending webs 114 so to allow air to freely pass through guide 90 in the regions surrounding web 114. Although needle 106 is hollow and has a sharpened tip 108, tip 108 is sealed. However, needle has a radially extending opening 116 through which air can flow from open end 107 of needle 106.

The embodiment of inhaler 2 shown in FIG. 3A is in the pre-use condition with cap 8 in place but without pharmaceutical cartridge 12 mounted within interior 14 of body 10. FIG. 3B illustrates inhaler 2 with cap 8 removed and cartridge 12 mounted within interior 14 at mouthpiece end 16. Pharmaceutical cartridge 12 includes a cylindrical body 118 sized to fit within interior 14. Body 118 has a radially extending pin 120 which fits within L-shaped locking slot 121 formed in body 10. Pharmaceutical cartridge 12 also includes a mouthpiece assembly 122 configured to mount to mouthpiece end 16. Mouthpiece assembly 122 includes a particulate filter 124 sized to prevent large particles from being inhaled into the user's mouth. Mouthpiece assembly 122 also provides inhaler 2 with a replaceable external mouthpiece surface 126 for enhanced cleanliness.

Body 118 includes three radially extending webs 128 shaped, sized and positioned similarly to webs 114. Webs 128 support a central hub 130 at an end 132 of body 118. Central hub 130 is sized to hold one end of a pharmaceutical-containing capsule 133. Capsule 133 is positioned so that sharpened tip 108, which passes through a central bore 134 in hub 130, pierces capsule 133 when pharmaceutical cartridge 12 is mounted into interior 14 of body 10.

End 132 of body 118 has a cut out or cam surface 136 positioned to engage tip 94 of return rod 84. That is, when body 118 is initially mounted into interior 14 with pin 120 within L-shaped slot 121, tip 94 contacts a position 138 at one end of cam surface 136. This forces return rod 84 in the direction of arrow 54, thus ensuring trigger disc 80 is at the sealed position of FIG. 3D. As body 118 is rotated within interior 14 with pin 120 moving along the circumferentially extending portion 140 of slot 121, tip 94 of return rod 84 becomes aligned with a recessed position 142 along cam surface 136. This permits axial play of rod 84 to permit the axial movement of trigger disc 80 in the direction opposite arrow 54 when the user inhales on mouthpiece assembly 122. Doing so creates a partial vacuum within the interior 144 of body 118; this moves trigger disc 80 in the direction opposite arrow 54, thus pulling open end 76 through O-ring 62 to create a fluid path between hollow interior 26 and the inside of capsule 133. The result of this is shown in FIG. 3E and is discussed below.

Figure 2:
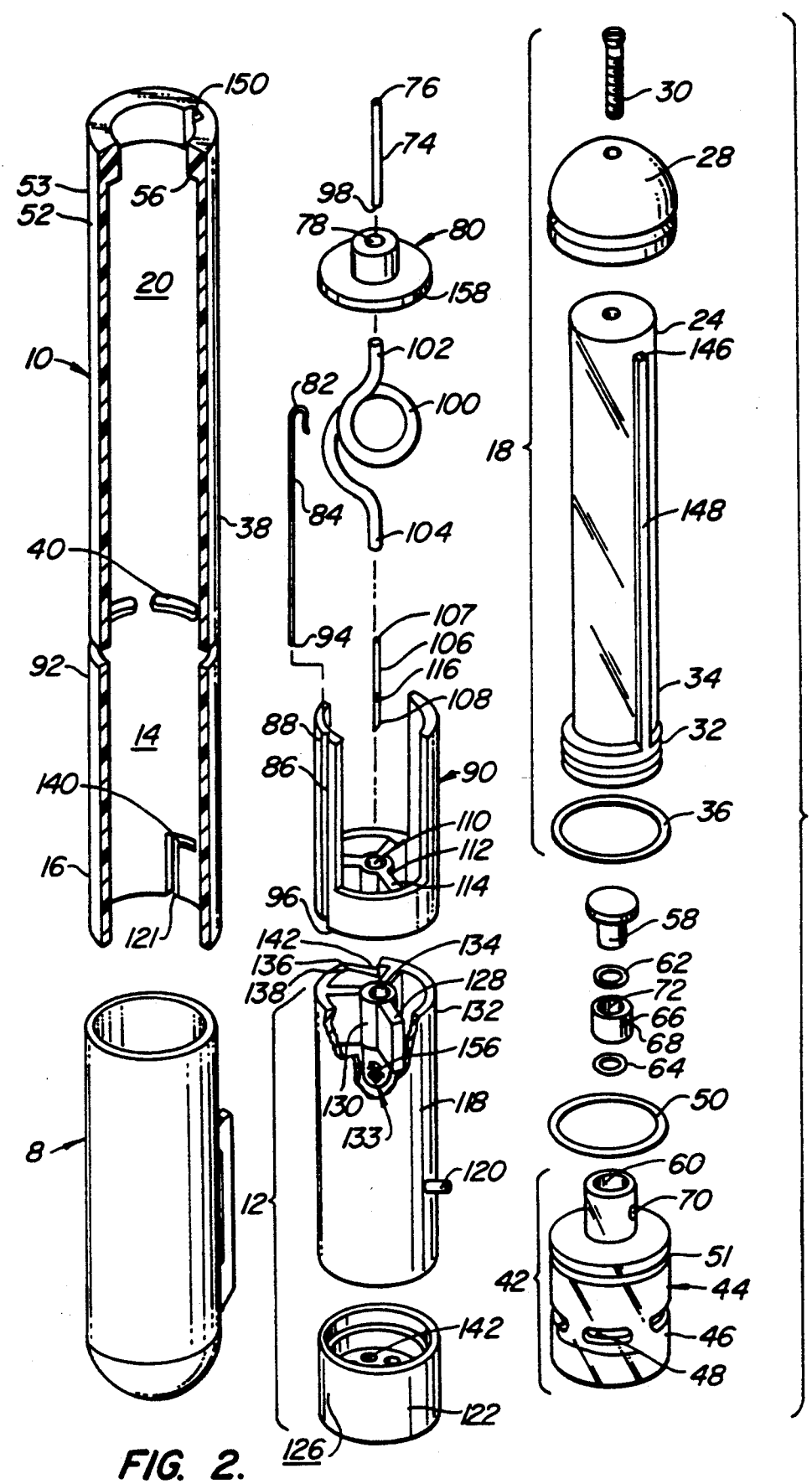
FIG. 2 is an exploded isometric view of the inhaler of FIG. 1, together with a pharmaceutical cartridge.

Inhaler 2 is designed to be used so that of the components shown in FIG. 2, pharmaceutical cartridge 12 is replaceable between each use. Thus, the user normally will keep inhaler 2 in the configuration of FIG. 2 with cap 8 mounted to mouthpiece end 16 for cleanliness. If desired, cap 8 may be extended so to cover openings 40 to minimize contamination of the interior 14 of body 10. Likewise, vent 52 could be a sealable vent as well.

To use inhaler 2, cap 8 is removed and a cartridge 12 is inserted into interior 14 of body 10 at open mouthpiece end 16 with pin 120 engaging slot 121. Doing so causes sharpened tip 108 to pierce capsule 133. If trigger disc 80 is not in the position of FIG. 3A, inserting body 118 fully into interior 14 causes end 82 of return rod 84 to push trigger disc from the position of FIG. 3E to the position of FIG. 3B. This causes open end 76 of hollow tube 74 to pass within and be sealed by O-ring 62. The user then pulls on pull knob 28 to pull plunger 18 to the position of FIG. 3C allowing air to enter cylinder 20 as indicated in FIG. 3C. Plunger 18 is then returned to the position of FIG. 3D and is locked into place by rotating plunger 18 so that the end 146 of a guide rib 148 is no longer aligned with slot 150, but abuts against shoulder 56 as shown in FIG. 3D. This creates a volume of pressurized air in hollow interior 26.

Figure 3E:
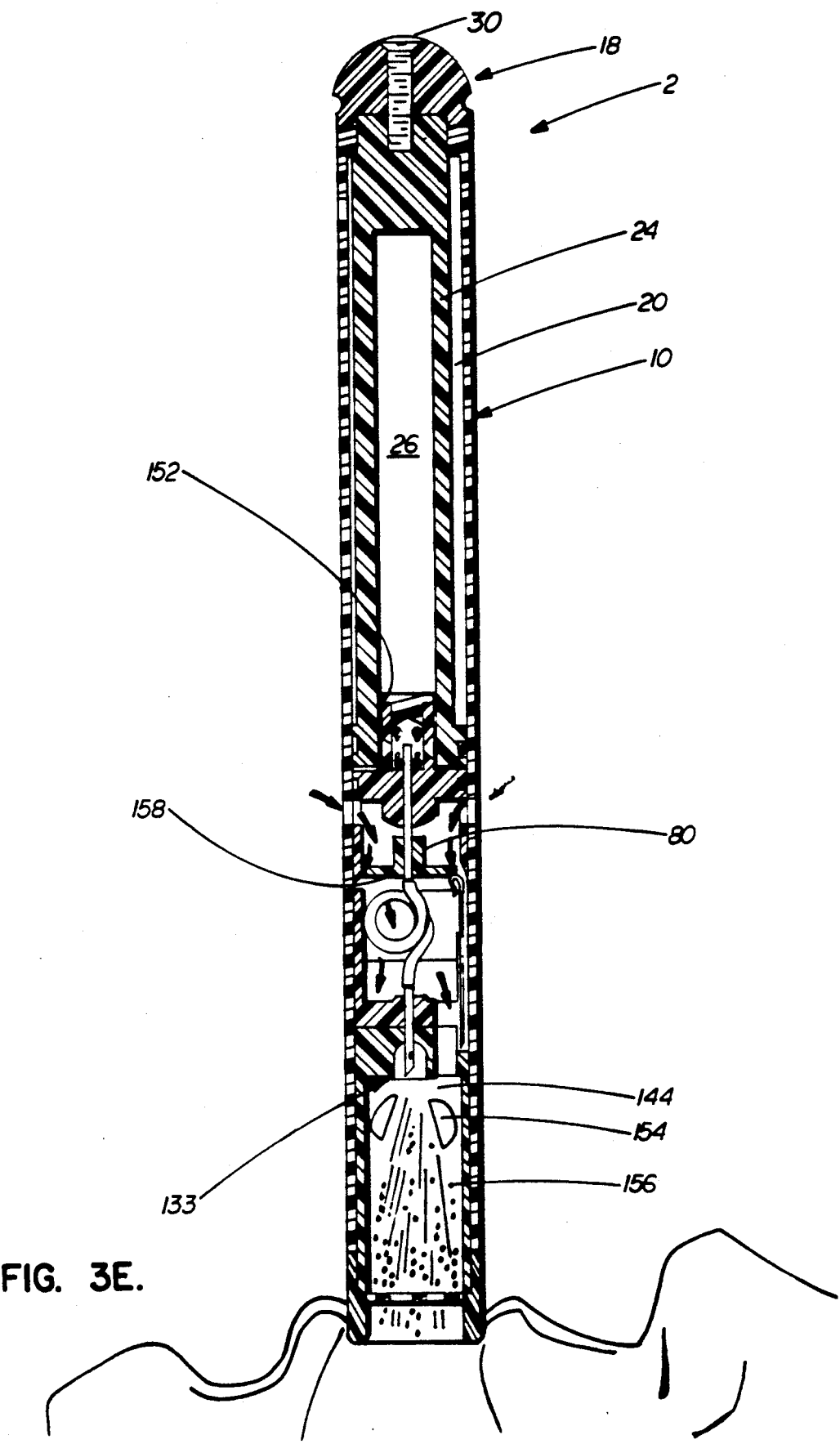
FIG. 3E illustrates the inhaler of FIG. 3D immediately after the user has placed the mouthpiece region of the inhalation chamber in the user's mouth and inhaled, thus opening an air pathway from the air pressurization chamber to the interior of the pharmaceutical capsule which creates a rush of pressurized air within the capsule to blow off the end of the capsule and cause the powdered pharmaceutical to be entrained into a flow of air which is being inhaled into the user's lungs.

Finally, as shown in FIG. 3E, the user places mouthpiece assembly 122 in his or her mouth and inhales. This creates a partial vacuum within interior 144, thus causing trigger disc 80 to move from the position of FIG. 3D to the position of FIG. 3E. This pulls hollow tube 74 from the position of FIG. 3D to the position of FIG. 3E which permits the pressurized air within interior 26 to pass along a gap 152 between valve housing 44 and hollow interior 26 of stem 24, through opening 70, 68, into open end 76, through hollow tube 74, flexible tube 100, hollow needle 106 and out radial opening 116. This sudden pressurization of the interior of capsule 133 causes the end 154 of capsule 133 to be essentially blown open as suggested in FIG. 3. This helps to propel powdered pharmaceutical 156 into the user's mouth via an air stream created by the pressurized air within hollow interior 26. Nonpressurized air passes through openings 40, 48, past the edge 158 of trigger disc 80, between fingers 88 of guide 90 and past webs 114, 128. This nonpressurized air mixes with the pressurized air from interior 26 and with pharmaceutical 156; the combination is inhaled into the user's mouth and lungs.

After use, the user removes pharmaceutical cartridge 12 by first rotating the cartridge within case 10 and then removing the cartridge axially from the case. Doing so causes tip 94 of return rod 84 to ride along cam surface 136 to return trigger disc 80 to the position of FIG. 3A.

Flexible tube 100 is configured the way it is shown to provide an efficient flow path, but also allow trigger disc 80 to be relatively freely movable when subjected to a partial vacuum created by the user.

Other types of valving assemblies could be used to connect pressurization chamber to the pharmaceutical-containing region. In the preferred embodiment, the pharmaceutical being contained within a capsule 133 housed within hub 130. However, by having the valve assembly triggered by the mere act of inhaling on the inhaler, accidental discharge can be all but eliminated; timing problems are automatically eliminated as well. In the preferred embodiment, a supply of pressurized air is created within hollow interior 26 of stem 24 through the reciprocation of plunger 18. However, instead of using vent 52 to allow air to enter cylinder 20, a check valve mounted at or near pull knob 28 could be used to couple cylinder 20 with the ambient environment; doing so would allow air to freely pass into the cylinder when the plunger is pulled, but is prevented from escaping when the plunger is returned back into body 10. Pharmaceutical cartridge 12 preferably includes the replaceable mouthpiece assembly 122, as well as replaceable body 118, along which the pharmaceutical 156 passes on its way into the user's mouth. While replacing the internal surfaces along which the pharmaceutical passes, substantially achieved using replaceable body 118, is an important aspect of the invention, the invention could be practiced without replacing the external surfaces of the mouthpiece since they can be easily wiped clean. Although it is generally preferred that a pharmaceutical cartridge be mounted within body 10 just before use (because capsule 133 is pierced by tip 108 of hollow needle 106), in some cases this may not be necessary.

Other modifications and variations can be made to this closed embodiment without departing from the subject or the invention as defined in the following claims. For example, the invention has been described with reference to powdered pharmaceuticals. However, the invention could be practiced using other flowable, dispersable pharmaceuticals, such as liquid pharmaceuticals, as well.

What is claimed is:

1. A pharmaceutical inhaler comprising:
   an air pressurization chamber having an air vent fluidly coupling the air pressurization chamber to outside air for permitting a quantity of air into the air pressurization chamber;
   means for pressurizing the quantity of air within the air pressurization chamber;
   an inhalation chamber including a mouthpiece region and a pharmaceutical region containing the pharmaceutical;
   an air flow path fluidly coupling the air pressurization chamber and the pharmaceutical region of the inhalation chamber; and
   an activating mechanism having an open position and a closed position and being operably positioned along the air flow path, the activating mechanism fluidly isolating the pressurization and inhalation chambers along the air flow path when in the closed position and fluidly coupling the pressurization and inhalation chambers when in the open position.

2. The inhaler of claim 1 wherein the gas pressurizing means includes a piston and stem.

3. The inhaler of claim 1 wherein the inhalation chamber is at least partially defined by a body having an inside surface.

4. The inhaler of claim 3 wherein the inhalation chamber includes replaceable means, replaceably mountable within the body, for lining the inside surface of the body between the pharmaceutical region and the mouthpiece region.

5. The inhaler of claim 4 wherein the replaceable lining means includes the pharmaceutical region.

6. The inhaler of claim 5 wherein the replaceable lining means includes means for supporting a pierceable capsule containing the pharmaceutical.

7. The inhaler of claim 6 wherein the fluidly coupling means includes a hollow needle mounted within the inhalation chamber and positioned to pierce the capsule when the replaceable lining means is mounted within the body.

8. A pharmaceutical inhaler comprising:
a gas pressurization chamber, including means for pressurizing a gas within pressurization chamber;
an inhalation chamber including a mouthpiece region, and a pharmaceutical region containing the pharmaceutical;
means for fluidly coupling the pressurization chamber to the pharmaceutical region when a user inhales through the mouthpiece region, whereby pressurized gas within the pressurization chamber flows through the fluidly coupling means to the pharmaceutical at the pharmaceutical region for inhalation of the pharmaceutical and the gas through the mouthpiece region and into the user's body; and
the fluidly coupling means including a trigger disc movable between a first position, at which the pressurization chamber is fluidly coupled to the pharmaceutical region, and a second position, at which the pressurization chamber is fluidly isolated from the pharmaceutical region, the trigger disc being movable from the second position to the first position upon inhalation on the mouthpiece region by the user.

9. The inhaler of claim 8 wherein the replaceable lining means includes means for moving the trigger disc from the first position to the second position.

10. The inhaler of claim 9 wherein the trigger disc moving means includes a cam surface and a return rod movably mounted relative to the body, the return rod having a first end engageable with the cam surface and a second end engageable with the trigger disc.

11. The inhaler of claim 9 wherein the fluidly coupling means includes a hollow tube connected to and movable with the trigger disc, the hollow tube having an open end, the fluidly coupling means including means for sealing the open end of the hollow tube from the pressurized gas within the pressurization chamber when the trigger disc is at the second position and for fluidly coupling the open end of the hollow tube with the pressurized gas within the pressurization chamber when the trigger disc is at the first position.

12. A powdered pharmaceutical inhaler comprising:
an air pressurization chamber having a sealable air vent fluidly coupling the air pressurization chamber to outside air for permitting a chosen quantity of air into the air pressurization chamber;
means for pressurizing the chosen quantity of air within the air pressurization chamber while keeping the air vent sealed;
an inhalation chamber at least partially defined by a body having an inside surface, the inhalation chamber including:
a mouthpiece region; and
a pharmaceutical region containing the powdered pharmaceutical;
replaceable means, replaceably mountable within the body, for lining the inside surface of the body between the pharmaceutical region and the mouthpiece region, the replaceable means including means for supporting a pierceable capsule containing the powdered pharmaceutical; and
means for fluidly coupling the pressurization chamber to the pharmaceutical region when a user inhales through the mouthpiece region, the fluidly coupling means including a hollow needle mounted within the inhalation chamber and positioned to pierce the capsule when the replaceable lining means is mounted within the body whereby pressurized gas within the pressurization chamber flows through the fluidly coupling means to the powdered pharmaceutical at the pharmaceutical region for inhalation of the powdered pharmaceutical and the gas through the mouthpiece region and into the user's body.

13. A pharmaceutical inhaler comprising:
an air pressurization chamber having a sealable air vent fluidly coupling the air pressurization chamber to outside air for permitting a chosen quantity of air into the air pressurization chamber;
means for pressurizing the chosen quantity of air within the air pressurization chamber while keeping the air vent sealed;
an inhalation chamber at least partially defined by a body having an inside surface, the inhalation chamber including a mouthpiece region, a pharmaceutical region containing the pharmaceutical, and replaceable means, replaceably mounted within the body, for lining the inside surface of the body between the pharmaceutical region and the mouthpiece region; and
means for fluidly coupling the air pressurization chamber to the pharmaceutical region, whereby pressurized air within the pressurization chamber flows through the fluidly coupling means to the pharmaceutical at the pharmaceutical region for inhalation of the pharmaceutical and the air through the mouthpiece region and into the user's body.

14. The pharmaceutical inhaler of claim 13 wherein the fluidly coupling means includes an inhalation chamber pressure-sensitive mechanism which moves from the closed position to the open position when the user inhales on the mouthpiece.

15. A pharmaceutical inhaler comprising:
an air pressurization chamber having an air vent fluidly coupling the air pressurization chamber to outside air for permitting a quantity of air into the air pressurization chamber;
means for pressurizing the quantity of air within the air pressurization chamber;
an inhalation chamber including a mouthpiece region, and a pharmaceutical region containing the pharmaceutical;
an air flow path fluidly coupling the air pressurization chamber and the pharmaceutical region of the inhalation chamber; and
an activating mechanism operably positioned along the air flow path having an open position and a closed position, the activating mechanism fluidly isolating the pressurization and inhalation chambers along the air flow path when in the closed position and fluidly coupling the pressurization and inhalation chambers along the air flow path when in the open position, the activating mechanism being an inhalation chamber pressure-sensitive mechanism which moves from the closed position to the open position when the use inhales on the mouthpiece.

16. A pharmaceutical inhaler comprising:

a source of pressurized gas having a gas outlet;

an inhalation chamber including a mouthpiece region and a pharmaceutical region containing the pharmaceutical;

a fluid flow path fluidly coupling the gas outlet and the pharmaceutical region of the inhalation chamber; and an inhalation pressure sensitive activating mechanism having an open position, a closed position, and being operably positioned along the fluid flow path, the activating mechanism fluidly isolating the gas outlet and inhalation chamber along the fluid flow path when in the closed position and fluidly coupling the gas outlet and the inhalation chamber when in the open position, the activating mechanism being urged into the open position when a user inhales through the mouthpiece region.

* * * * *